United States Patent [19]

Yamada et al.

[11] Patent Number: 4,609,626
[45] Date of Patent: Sep. 2, 1986

[54] METHOD FOR PRODUCING S-ADENOSYL-L-HOMOCYSTEINE HYDROLASE

[75] Inventors: Hideaki Yamada; Sakayu Shimizu, both of Kyoto; Shozo Shiozaki, Kamakura, all of Japan

[73] Assignee: Nippon Zeon Co., Ltd., Tokyo, Japan

[21] Appl. No.: 634,208

[22] Filed: Jul. 25, 1984

[30] Foreign Application Priority Data

Jul. 29, 1983 [JP] Japan .................................. 58-139134

[51] Int. Cl.$^4$ ........................... C12N 9/14; C12R 1/01; C12R 1/05; C12R 1/06; C12R 1/065; C12R 1/465; C12R 1/15; C12R 1/20; C12R 1/32; C12R 1/29; C12R 1/365; C12R 1/38
[52] U.S. Cl. ..................................... 435/195; 435/822; 435/829; 435/830; 435/843; 435/850; 435/867; 435/872; 435/874; 435/831; 435/863; 435/886
[58] Field of Search .......................................... 435/195

[56] References Cited

PUBLICATIONS

Journal of Bacteriology, vol. 112, No. 1, pp. 569–575, Oct. 1982.
Canadian Journal of Biochemistry, vol. 53, pp. 312–319 (1975).
Eur. J. Biochemistry, vol. 141, pp. 385–392 (1984).
Guranowski, et al., "Adenosylhomocysteinase from Yellow Lupin Seeds," Eur. J. Biochem., 80, (1977), pp. 517–523.
Fujioka, et al., "S-Adenosylhomocysteine Hydrolase from Rat Liver," J. Biol. Chem., vol. 256, No. 4, (1981), pp. 1631–1635.

*Primary Examiner*—Lionel M. Shapiro
*Attorney, Agent, or Firm*—Sherman and Shalloway

[57] ABSTRACT

A method for producing S-adenosyl-L-homocysteine hydrolase, which comprises cultivating a microorganism having the ability to produce S-adenosyl-L-homocysteine hydrolase within its cells in a nutrient medium to accumulate said hydrolase in the cells, said microorganism being a bacterium belonging to the genera Alcaligenes, Pseudomonas, Acinetobacter, Arthrobacter, Enterobacter, Rhodopseudomonas, Agrobacterium, Micrococcus, Corynebacterium, Brevibacterium, Chromobacterium, Xanthomonas, Flavobacterium, Cellulomonas, Azotobacter and Protaminobacter, or an actinomycete belonging to the genera Streptomyces, Mycobacterium, Nocardia, Streptoverticillium, Micromonospora, Micropolyspora, Streptosporangium and Microellobosporia; and then recovering S-adenosyl-L-homocysteine hydrolase from the cells.

7 Claims, No Drawings

METHOD FOR PRODUCING S-ADENOSYL-L-HOMOCYSTEINE HYDROLASE

This invention relates to a novel process for producing S-adenosyl-L-homocysteine hydrolase (EC 3311).

S-adenosyl-L-homocysteine hydrolase (to be abbreviated as SAHase) is an imporant enzyme which relates to the active methyl cycle in vivo. It is known to be involved in the following reaction.

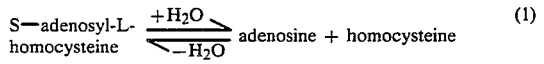

$$\text{S-adenosyl-L-homocysteine} \underset{-H_2O}{\overset{+H_2O}{\rightleftarrows}} \text{adenosine} + \text{homocysteine} \quad (1)$$

The existence of SAHase is known in eucaryotes such as animals, plants and yeasts. A pure authentic sample has been taken out from the rat liver, for example, and its enzymatic properties have been examined [see, for example, Eur. J. Biochem., 80, 517 (1977) and J. Biol. Chem., 256, 1631 (1981)]. It has however been believed that SAHase does not exist in procaryotes such as *Escherichia coli*, and therefore, there has been a great restriction on the source of its supply.

In the course of investigating the synthesis of S-adenosyl-L-homocysteine (to be referred to as SAH) by procaryotes, we have found unexpectedly that certain bacteria have the ability to synthesize SAH from adenosine (AdR for short) and homocysteine (Hcy for short).

Further investigations have led to the discovery that SAHase whose existence in procaryotes has previously been denied does exist in certain procaryotes, and can be easily collected from their microbial cells.

According to this invention, there is provided a method for producing SAHase, which comprises cultivating a microorganism having the ability to produce SAHase within its cells in a nutrient medium to accumulate SAHase in the cells, said microorganism being a bacterium belonging to the genera Alcaligenes, Pseudomonas, Acinetobacter, Arthrobacter, Enterobacter, Rhodopseudomonas, Agrobacterium, Micrococcus, Corynebacterium, Brevibacterium, Chromobacterium, Xanthomonas, Flavobacterium, Cellulomonas, Azotobacter and Protaminobacter, or an actinomycete belonging to the genera Streptomyces, Mycobacterium, Nocardia, Streptoverticillium, Micromonospora, Micropolyspora, Streptosporangium and Microellobosporia; and then recovering SAHase from the cells.

The microorganism having the ability to produce SAHase in this invention may be any of the microorganisms belonging to the genera stated above and having the ability to accumulate SAHase in the cells. Specific examples of the bacterium include *Alcaligenes faecalis* (IFO 12669), *Pseudomonas putida* (IFO 12966), *Acinetobacter calcoaceticus* (IFO 12552), *Arthrobacter globiformis* (IFO 12137), *Enterobacter cloacae* (IFO 13535), *Rhodopseudomonas spheroides* (IFO 12203), *Agrobacterium tumefaciens* (IFO 13265), *Micrococcus luteus* (IFO 3333), *Corynebacterium fascians* (IFO 12077), *Brevibacterium protophormiae* (IFO 12128), *Chromobacterium iodinum* (IFO 3558), *Xanthomonas campestris* (IFO 13303), *Flavobacterium gasogenes* (IFO 12065), *Cellulomonas flavigena* (IFO 3753), *Azotobacter vinelandii* (IFO 12018) and *Protaminobacter ruber* (IFO 3708). Specific examples of the actinomycete include *Streptomyces hygroscopicus* (IFO 3192), *Mycobacterium phlei* (IFO 3158), *Nocardia asteroides* (IFO 3424), *Streptoverticillium kentuchense* (IFO 12880), *Micromonospora coerulea* (IFO 13504), *Micropolyspora angiospora* (IFO 13155), *Streptosporangium roseum* (IFO 3776), and *Microellobosporia violacea* (IFO 12517). Natural and artificial mutants of these microorganisms may equally be used so long as they have the ability to produce SAHase.

In practicing the present invention, the SAHase-producing microorganism is first cultivated. The cultivation may be liquid cultivation or solid surface cultivation. Industrially, it is advantageous to inoculate the SAHase-producing microorganism in a liquid medium and cultivate it aerobically with aeration and stirring. Nutrient sources for the culture medium may be carbon sources, nitrogen sources, inorganic salts, trace organic nutrient sources, etc. which are normally used in the cultivation of microorganisms, and can be properly chosen depending upon the type of the microorganism to be cultivated. The cultivation temperature may be properly chosen within a range in which the microorganism grows to produce SAHase. Generally, it is from 15° to 50° C. The pH of the culture medium is usually 3 to 10. The cultivation time may be properly chosen depending upon the type of the microorganism. The cultivation may be terminated at a suitable time when the activity of SAHase reached a maximum. In the resulting cultivation product, SAHase is accumulated in the microorganism cells.

There is no particular restriction on the method of obtaining a solution containing crude SAHase by extracting SAHase from the resulting cultivation product. For example, a solution containing crude SAHase is obtained by subjecting the culture broth to solid-liquid separation, optionally suspending the resulting wet cells in a phosphate buffer or a Tris-HCl buffer, extracting SAHase from the cells by a suitable combination of cell treating means including lysozyme treatment, ultrasonication, treatment by a French press, a grinding treatment with glass beads, quartz sand, etc. and lysis with a surface-active agent.

Purified SAHase can be obtained by subjecting the resulting solution containing crude SAHase to methods known as isolation and purification means for proteins and enzymes. Specifically, such isolation and purification means include ammonium sulfate fractionation, ion-exchange chromatography, adsorptive chromatography, and gel filtration. As required, these techniques may be properly combined.

The SAHase so obtained is an enzyme which catalyzes the reaction shown by the above reaction scheme (I), and is useful as a reagent for clinical examination and for research work.

The following Examples illustrate the present invention more specifically. All percentages in these examples are by weight unless otherwise specified.

The method of measuring the enzyme activity of SAHase is as follows:

(1) Method of measuring enzyme activity (a) Enzyme activity in the reaction of synthesizing SAH from AdR and Hcy Ten microliters of an enzyme solution is added to 1 ml of a reaction solution containing 5 micromoles of AdR, 10 miromoles of DL-Hcy and 50 micromoles of phosphate buffer (pH 8.0), and they are reacted in an atmosphere of nitrogen at 37° C. for 15 minutes. Then, the reaction is stopped by adding 0.1 ml of 30% perchloric acid. Then, 0.9 ml of 0.5M phosphate buffer (pH 7.0) was added to the reaction mixture. The resulting precipitate is removed by centrifugal separation. The supernatant obtained is analyzed by high-performance liquid chromatography (Model 638-30 made by Hitachi Limited; column Cosmocil 5C$_{18}$; eluent 0.2M KH$_2$PO$_4$/methanol=90/10 (V/v); detector UV 260 nm) to determine the amount of SAH produced. The SAH synthesizing enzyme activity is expressed in units. One unit is defined as the amount of the enzyme which is required to form 1 micromole of SAH per minute.

(b) Enzyme activity in SAH hydrolysis reaction

SAH is reacted with SAHase, and the resulting AdR is converted to inosine in the presence of an excess of adenosine deaminase. The speed of the decrease of the absorbance at 265 nm at this time is measured. Specifically, 475 microliters of 10 mM phosphate buffer, 10 microliters of 2.5 mM SAH, 5 microliters of adenosine deaminase (Type III produced by Sigma Company) and 10 microliters of an enzyme solution are reacted at 25° C., and the speed of the decrease of the absorbance at 265 nm at this time is measured to determine the amount of SAH hydrolyzed. The SAH hydrolysis enzyme activity is expressed in units. One unit is defined as the amount of the enzyme which is required to hydrolyze 1 micromole of SAH per minute.

(2) Activity (i) Produces 1 mole of SAH from 1 mole of AdR and 1 mole of Hcy.

(ii) Produces 1 mole of AdR and 1 mole of Hcy from 1 mole of SAH and 1 mole of water.

(3) Optimum pH

Various reaction solutions are prepared in the same way as in the method of measuring the enzyme activity in (1) above except that the phosphate buffer (pH 8.0) is replaced by sodium acetate buffers having a pH of 3.5 to 5.5, potassium phosphate buffers having a pH of 5.5 to 8.0, Tris-HCl buffers [i.e., tris(hydroxymethyl-)aminomethane-hydrochloride] having a pH of 8.0 to 9.5, and sodium phosphate buffers having a pH of 9.5 to 12.0. The activities of the reaction solutions are respectively measured, and the optimum pH is determined.

(4) pH stability

The enzyme solution is added to the various buffers used in measuring the optimum pH in (3) above, and the mixtures are left to stand at 37° C. for 10 minutes. The residual rate of the SAHase activity is measured.

(5) Heat stability

The enzyme solution is treated for 10 minutes at a temperature of 20°, 30°, 40°, 45°, 50°, 55° and 60° C. respectively, and its residual activity is measured.

(6) Km value

Km values for SAH, AdR and DL-Hcy are measured.

EXAMPLE 1

*Alcaligenes faecalis* (IFO 12669) was cultivated at 28° C. for 24 hours in an agar slant culture medium (pH 7.0) composed of 1 g/dl of glucose, 1.5 g/dl of peptone, 0.3 g/dl of yeast extract, 0.3 g/dl of K$_2$HPO$_4$, 0.2 g/dl of NaCl, 0.02 g/dl of MgSO$_4$.7H$_2$O and 2 g/dl of agar. One platinum loopful of the culture broth was inoculated in 10 ml of a heat sterilized liquid medium adjusted to pH 7.0 and composed of 1 g/dl of glucose, 1.5 g/dl of peptone, 1 g/dl of yeast extract, 0.3 g/dl of K$_2$HPO$_4$, 0.2 g/dl of NaCl and 0.02 g/dl of MgSO$_4$.7H$_2$O, and cultivated at 28° C. for 24 hours. The culture broth was inoculated in forty 2-liter Sakaguchi flasks each containing 500 ml of a heat sterilized liquid medium having the same composition as the liquid medium used for obtaining the seed. Cultivation was carried out with shaking at 28° C. for 24 hours. After the cultivation, the culture broth was centrifuged to obtain cells.

The cells were suspended in 400 ml of 0.02M potassium phosphate buffer (pH 7.5) containing 0.5 mM dithiothreitol, and the suspension was ultrasonicated to extract SAHase. The insoluble materials were removed by centrifugal separation. Ammonium sulfate was added to 40% saturation to the resulting supernatant. The precipitate was removed by centrifugal separation. Ammonium sulfate was further added to the supernatant so that the final concentration was 60% saturation. The resulting precipitate containing SAHase was dissolved in 100 ml of 0.02M phosphate buffer (pH 7.5) containing 0.5 mM dithiothreitol. The solution was then dialyzed against 0.01M Tris-HCl buffer (pH 7.4) containing 0.5 mM dithiothreitol. The dialyzate was passed through a DEAE-Sephacell column (made by Pharmacia Company, diameter 5 cm, length 40 cm) which had been equilibrated with a 0.01M Tris-HCl buffer containing 0.5 mM dithiothreitol to adsorb SAHase on the column. The column was washed with the same buffer, and SAHase was eluted by providing a concentration gradient between the same buffer and a solution of 0.5 M of sodium chloride in the same buffer and gradually raising the concentration of sodium chloride. The eluted SAHase active fractions were collected, and those precipitated with 45–50% saturated ammonium sulfate were dissolved in 10 ml of 0.02M potassium phosphate buffer (pH 7.5) containing 0.5 mM dithiothreitol, and the solution was subjected to gel filtration on a Sephadex G200 (produced by Pharmacia Company) column which had been equilibratd with the same buffer. SAHase active fractions were collected, and those which were precipitated with 40–55% saturated ammonium sulfate were dissolved in 8 ml of 0.01M potassium phosphate buffer (pH 7.5) containing 0.5 mM dithiothreitol and 4M NaCl, and left to stand overnight at 5° C. to crystallize SAHase. The resulting crystals were recovered by centrifugal separation, and again dissolved in the same buffer. Ammonium sulfate was added to 40% saturation to recrystallize SAHase. There was obtained 60 mg of a sample of SAHase. The resulting sample had a specific activity of SAH synthesizing reaction of 2.81 U/mg, a specific activity in SAH hydrolyzing reaction of 0.54 U/mg, and a yield of 13.1% from the culture broth. The optimum pH of the enzyme in the SAH synthesizing reaction and the SAH hydrolyzing reaction was 8.0 to 10.0. Its pH stability was 6.5 to 10.0 and a heat stability of not more than 45° C. The Km values for SAH, AdR and DL-Hcy were 10 μM, 37 μM and 0.93 mM. Its isoelectric point was 4.7.

EXAMPLE 2

*Streptomyces hygroscopicus* (IFO 3192) was cultivated at 28° C. for 48 hours in an agar slant medium (pH 7.0) composed of 1 g/dl of peptone, 0.5 g/dl of meat extract, 0.1 g/dl of yeat extract, 0.5 g/dl of NaCl and 2 g/dl of agar. One platinum loopful of the culture broth was inoculated in 10 ml of a heat-sterilized liquid medium adjusted to pH 7.0 and composed of 1 g/dl of peptone, 0.5 g/dl of meat extract, 0.1 g/dl of yeast extract and 0.5 g/dl of NaCl, and cultivated at 28° C. for 48 hours. The culture broth was then inoculated in thirty 2-liter Sakaguchi flasks each containing 500 ml of a heat-sterilized liquid medium having the same composition as the liquid medium for obtaining the seed, and cultivated with shaking at 28° C. for 48 hours. After the cultivation, the culture broth was filtered to give cells.

The cells were suspended in 150 ml of 0.02M potassium phosphate (pH 7.5) containing 0.5 mM dithiothreitol. The suspension was then treated with glass beads to crush the cells, and the insoluble materials were removed by centrifugal separation. Ammonium sulfate was added to 40% saturation to the resulting supernatant. The precipitate was removed by centrifugal separation. Ammonium sulfate was further added to the supernatant so that the final concentration became 60% saturation. Thus, SAHase was precipitated. The precipitate was dissolved in 45 ml of 0.02M phosphate buffer (pH 7.5) containing 0.5 mM dithiothreitol. The solution was dialyzed against 0.01M Tris-HCl buffer containing 0.5 mM dithiothreitol. The dialyzate was passed through a DEAE-cellulose column (diameter 3 cm, length 30 cm) which had been equilibrated with 0.01M Tris-HCl buffer containing 0.5 mM dithiothreitol to adsorb SAHase on the column. The column was washed with the same buffer, and then SAHase was eluted by providing a concentration gradient between the same buffer and a solution of 0.5M sodium chloride in the same buffer and gradually increasing the concentration of sodium chloride. The eluted SAHase active fractions were collected, and those precipitated with 45–55% saturated ammonium sulfate were dissolved in 5 ml of 0.02M potassium phosphate buffer (pH 7.5) containing 0.5 mM dithiothreitol. The solution was subjected to gel filtration on a Sephadex G-200 column equilibrated with the same buffer. SAHase active fractions were collected, concentrated on an ultrafiltration membrane (Diaflo Membrane XM-50, a product of Amicon), and lyophilized to form 11 mg of a sample of SAHase.

The sample had a specific activity in SAH synthesizing reaction of 1.35 U/mg, a specific activity in SAH hydrolyzing reaction of 0.18 U/mg, and a yield from the culture broth of 26.3%. Its other enzymatic properties were almost equivalent to those in Example 1.

EXAMPLE 3

Cells obtained by the same method as in Example 1 except that each of the bacteria shown in Table 1 was used and only one Sakaguchi flask was used. The cells so cultivated and recovered were suspended in 10 ml of 0.02M potassium phosphate buffer (pH 7.5) containing 0.5 mM dithiothreitol. The suspension was ultrasonicated and centrifuged. The specific activity of the resulting SAHase was measured. The results are summarized in Table 1.

By purifying the above supernatant in the same way as in Example 1, SAHase having much the same enzymatc properties as SAHase obtained in Example 1 could be isolated.

TABLE 1

| Microorganism | Specific activity (U/ml) SAH synthesizing reaction | Specific activity (U/ml) SAH hydrolyzing reaction |
| --- | --- | --- |
| *Pseudomonas putida* (IFO 12996) | 0.53 | 0.030 |
| *Acinetobacter calcoaceticus* (IFO 12552) | 0.37 | 0.020 |
| *Arthrobacter globiformis* (IFO 12137) | 0.15 | 0.014 |
| *Enterobacter cloacae* (IFO 13535) | 0.09 | 0.014 |
| *Rhodopseudomonas spheroides* (IFO 12203) | 0.08 | 0.010 |
| *Agrobacterium tumefaciens* (IFO 13265) | 0.18 | 0.010 |
| *Micrococcus luteus* (IFO 3333) | 0.20 | 0.012 |
| *Corynebacterium faciens* (IFO 12077) | 0.09 | 0.011 |
| *Brevibacterium protophormiae* (IFO 12128) | 0.15 | 0.027 |
| *Chromobacterium iodinum* (IFO 3558) | 0.30 | 0.019 |
| *Xanthomonas campestris* (IFO 13303) | 0.14 | 0.011 |
| *Flavobacterium gasogenes* (IFO 12065) | 0.08 | 0.017 |
| *Cellulomonas flavigena* (IFO 3753) | 0.08 | 0.016 |
| *Azotobacter vinelandii* (IFO 12018) | 0.17 | 0.020 |
| *Protaminobacter ruber* (IFO 3708) | 0.16 | 0.013 |

EXAMPLE 4

Cells were obtained by the same method as in Example 2 except that each of the actinomycetes shown in Table 2 was used, and only one Sakaguchi flask was used. The cells so cultivated and recovered were suspended in 8 ml of 0.02M potassium phosphate buffer (pH 7.5) containing 0.5M dithiothreitol. The suspension was treated wtih glass beads to crush the cells. The insoluble materials were removed by centrifugal separation. The specific activity of SAHase in the resulting supernatant was measured, and the results are shown in Table 2.

By purifying the supernatant in the same way as in Example 2, SAHase having much the same enzymatic properties as SAHase obtained in Example 1 could be isolated.

TABLE 2

| Microorganism | Specific activity (U/ml) SAH synthesizing reaction | Specific activity (U/ml) SAH hydrolyzing reaction |
| --- | --- | --- |
| *Mycobacterium phlei* (IFO 3158) | 0.29 | 0.025 |
| *Nocardia asteroides* (IFO 3424) | 0.09 | 0.009 |
| *Streptoverticillium kentuchense* (IFO 12880) | 0.18 | 0.011 |
| *Micromonospora coerulea* (IFO 13504) | 0.10 | 0.010 |
| *Micropolyspora angiospora* (IFO 13155) | 0.21 | 0.018 |
| *Streptosporangium roseum* (IFO 3776) | 0.17 | 0.009 |
| *Microellobosporia violacea* (IFO 12517) | 0.16 | 0.012 |

What is claimed is:

1. A method for producing S-adenosyl-L-homocysteine hydrolase, which comprises cultivating a microorganism having the ability to produce S-adenosyl-L-homocysteine hydrolase within its cells in a nutrient medium to accumulate said hydrolase in the cells, said microorganism being a bacterium belonging to the genera Alcaligenes, Pseudomonas, Acinetobacter, Arthrobacter, Enterobacter, Rhodopseudomonas, Agrobacterium, Micrococcus, Corynebacterium, Brevibacterium, Chromobacterium, Xanthomonas, Flavobacterium, Cellulomonas, Azotobacter and Protaminobacter, or an actinomycete belonging to the genera Streptomyces, Mycobacterium, Nocardia, Streptoverticillium, Micromonospora, Micropolyspora, Streptosporangium and Microellobosporia; and then recovering S-adenosyl-L-homocysteine hydrolase from the cells.

2. The method of claim 1 wherein the cultivation is carried out at a temperature of 15° to 50° C. and a pH of 3 to 10.

3. The method of claim 1 wherein the cultivation is carried out aerobically in a liquid medium.

4. The method of claim 1 wherein the microorganism having the ability to produce S-adenosyl-L-homocysteine hydrolase is the bacterium.

5. The method of claim 1 wherein the bacterium belongs to the genus Alcaligenes, Pseudomonas, Acinetobacter or Chromobacterium.

6. The method of claim 1 wherein the microorganism having the ability to produce S-adenosyl-L-homocysteine hydrolase is the actinomycete.

7. The method of claim 1 wherein the actinomycete belongs to the genus Streptomyces, Mycobacterium or Micropolyspora.

* * * * *